US005209226A

United States Patent [19]

Goodley

[11] Patent Number: 5,209,226

[45] Date of Patent: May 11, 1993

[54] UNDERWATER RESPIRATORY DEVICE

[76] Inventor: Mark D. Goodley, 3120 Ryan Dr., Escondido, Calif. 92025

[21] Appl. No.: 846,242

[22] Filed: Jan. 17, 1992

[51] Int. Cl.[5] .................. A61M 16/06

[52] U.S. Cl. .................. 128/205.25; 128/204.18; 128/207.14; 128/207.17; 128/206.24; 367/131; 181/18

[58] Field of Search .................. 128/200.24, 201.19, 128/202.27, 204.18, 205.24, 207.14, 207.17, 205.25, 206.24, 206.21; 181/21, 18; 367/131, 132

[56] References Cited

U.S. PATENT DOCUMENTS

| | | | |
|---|---|---|---|
| 2,857,911 | 10/1958 | Bennett | 128/206.24 |
| 3,347,230 | 10/1967 | Cupp | 128/201.19 |
| 4,071,110 | 1/1979 | Payne | 128/201.19 X |
| 4,527,657 | 7/1985 | Payne | 181/18 |
| 4,839,871 | 7/1989 | Massey | 367/132 |

FOREIGN PATENT DOCUMENTS

| | | | |
|---|---|---|---|
| 234118 | 4/1931 | Italy | 181/18 |
| 126368 | 6/1959 | U.S.S.R. | 128/201.19 |

*Primary Examiner*—Edgar S. Burr
*Assistant Examiner*—Eric P. Raciti
*Attorney, Agent, or Firm*—Ralph S. Branscomb

[57] ABSTRACT

An air supply system which communicates between the compressed air supply and the mouth of a scuba diver utilizes a sealing cup which surrounds the mouth to define a breathing/microphone chamber into which the diver can speak. In addition to this chamber into which the diver can breath, a mouthpiece on an airpipe which passes through the sealing cup can be quickly forced into the mouth for direct breathing through the mouth into the air tube, bypassing the breathing chamber defined by the sealing cup in the event this chamber becomes flooded.

11 Claims, 3 Drawing Sheets

Fig. 6
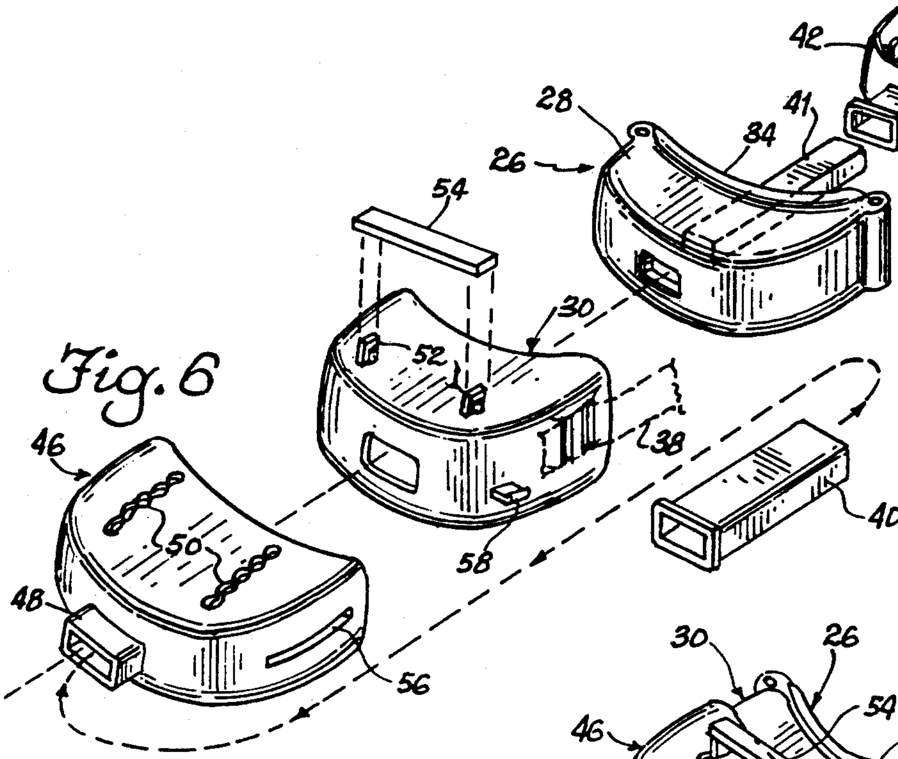
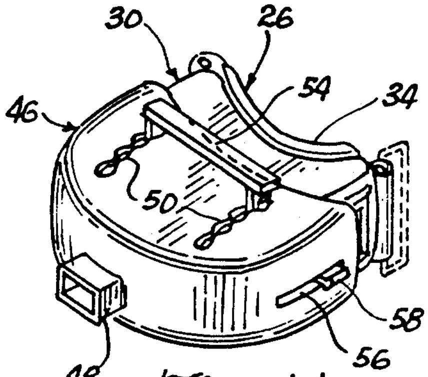
Fig. 7
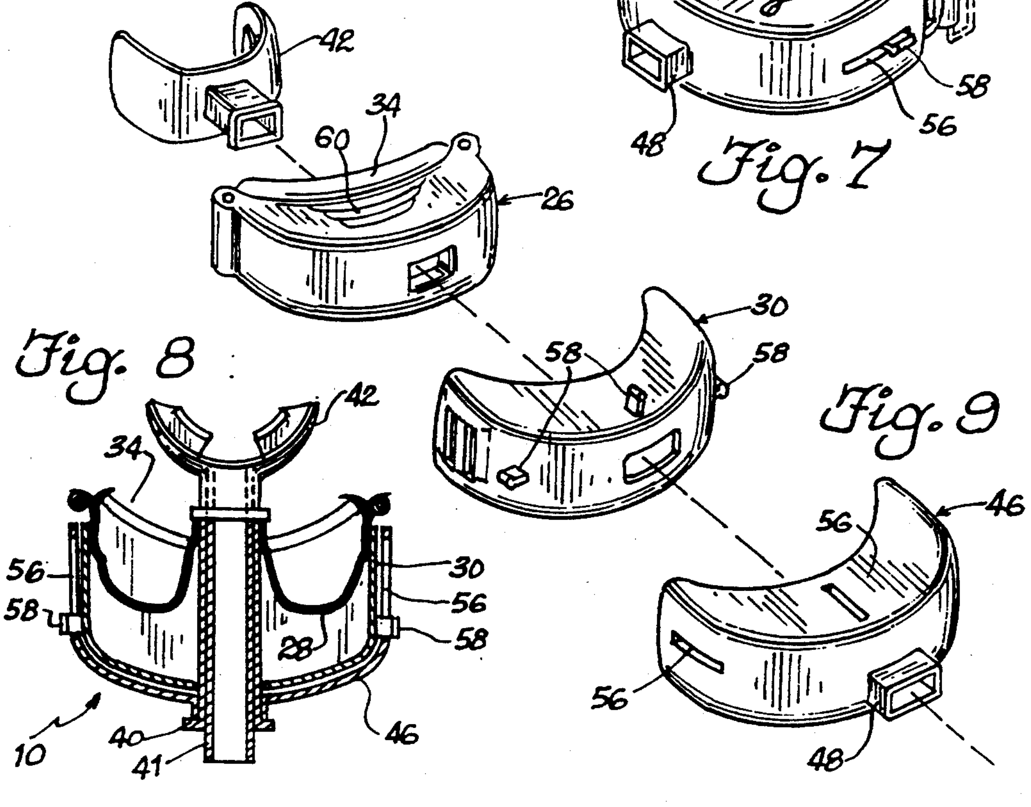
Fig. 8
Fig. 9

UNDERWATER RESPIRATORY DEVICE

BACKGROUND OF THE INVENTION

The invention is in the field of air supply systems for scuba divers, and particularly pertains to the problem of providing air to the diver in a safe and comfortable manner, while at the same time freeing the mouth so that the diver can speak into a microphone attached to a transmitter.

A diver without a microphone utilizes a mouthpiece which fits into the mouth and is gripped by the teeth, with a flange between the lips and teeth to securely hold the mouthpiece in place. This enables the natural, perfect sealing power of the lips to achieve the seal around the airpipe extending from the mouthpiece. This is a very effective time-tested manner of providing breathable air to the diver in a virtually fool-proof and fairly comfortable manner.

However, if the diver must communicate with other divers, a surface boat or a transponder bouy, clearly he must have freedom of movement of his mouth and jaw, so that the mouthpiece system is no longer acceptable.

There are currently several units on the market which solve this speaking/breathing problem by replacing the mouthpiece with a sealing cup which fits over the mouth, defining a breathing chamber into which the diver both breaths and speaks. However, when this is done, the naturally perfect sealing ability of the lips must be replaced by the sealing capability of a split rubber lip which seals the edges of the sealing cup against the flesh surrounding the mouth.

This system works as long as the seal holds, but should the diver bump against something and break the seal, the breathing chamber quickly fills with water and the diver is in trouble. There is no mechanism built into these systems that is effective in either preventing this from happening, or easily purging the water once it has entered the breathing chamber. These units are also uniformly bulky, uncomfortable and unattractive. They are held in place by a separate strap around the head which creates an uncomfortable, gangly situation for the diver inasmuch as he must also have his mask and mask strap on. No mouthpiece is provided in the event the unit becomes dislodged or the headstrap breaks. Further, because they are uniformly of one-piece construction, they do not accomodate the different-sized faces and mouths of different divers.

There is a need for a diver's breathing system which solves the above-stated problems, and in particular provides a safety system enabling the diver to quickly insert a mouthpiece into his mouth should the sealing cup which defines the breathing chamber become flooded.

SUMMARY OF THE INVENTION

The instant invention fullfills the above stated need and comprises a sealing cup which seals around the mouth, above the upper lip and across the chin and the sides of the mouth, but also has a rigid breathing tube which passes through the sealing cup, communicating from a forward air supply through the sealing cup to a mouthpiece which can be selectively pushed into the mouth of the user, or pulled back out into the breathing chamber of the sealing cup, permitting the diver to speak in an unfettered manner.

The airpipe serves as a stem upon which the outer frame of the sealing cup slides, so that this frame maintains the shape of the flexible diaphragm which defines the breathing chamber and seals around the mouth. The sealing cup is strapped to the head of the diver, so that the breathing pipe and stem moves in and out relative to the diver's face through the outer frame of the sealing cup carrying the mouthpiece with it, so that at all times the sealing cup seals around to the mouth of the user, whether the mouthpiece is pushed into the mouth, or is pulled out clear of the mouth to permit use of the microphone.

BRIEF DESCRIPTION OF THE DRAWINGS

FIG. 6 is an exploded perspective illustrating all of the parts of the breathing apparatus before they are bonded together;

FIG. 7 is a perspective view of the breathing cup seated in the outer shell illustrating the mutual detent and guide structure;

FIG. 9 is an exploded perspective view similar to that of FIG. 6 but illustrating the underside of the parts of the diving apparatus and FIG. 8 is a horizontal section taken through the apparatus as it would appear in the configuration of FIG. 2 with the mouthpiece received in the mouth.

DETAILED DESCRIPTION OF THE PREFERRED EMBODIMENT

Figure 1:
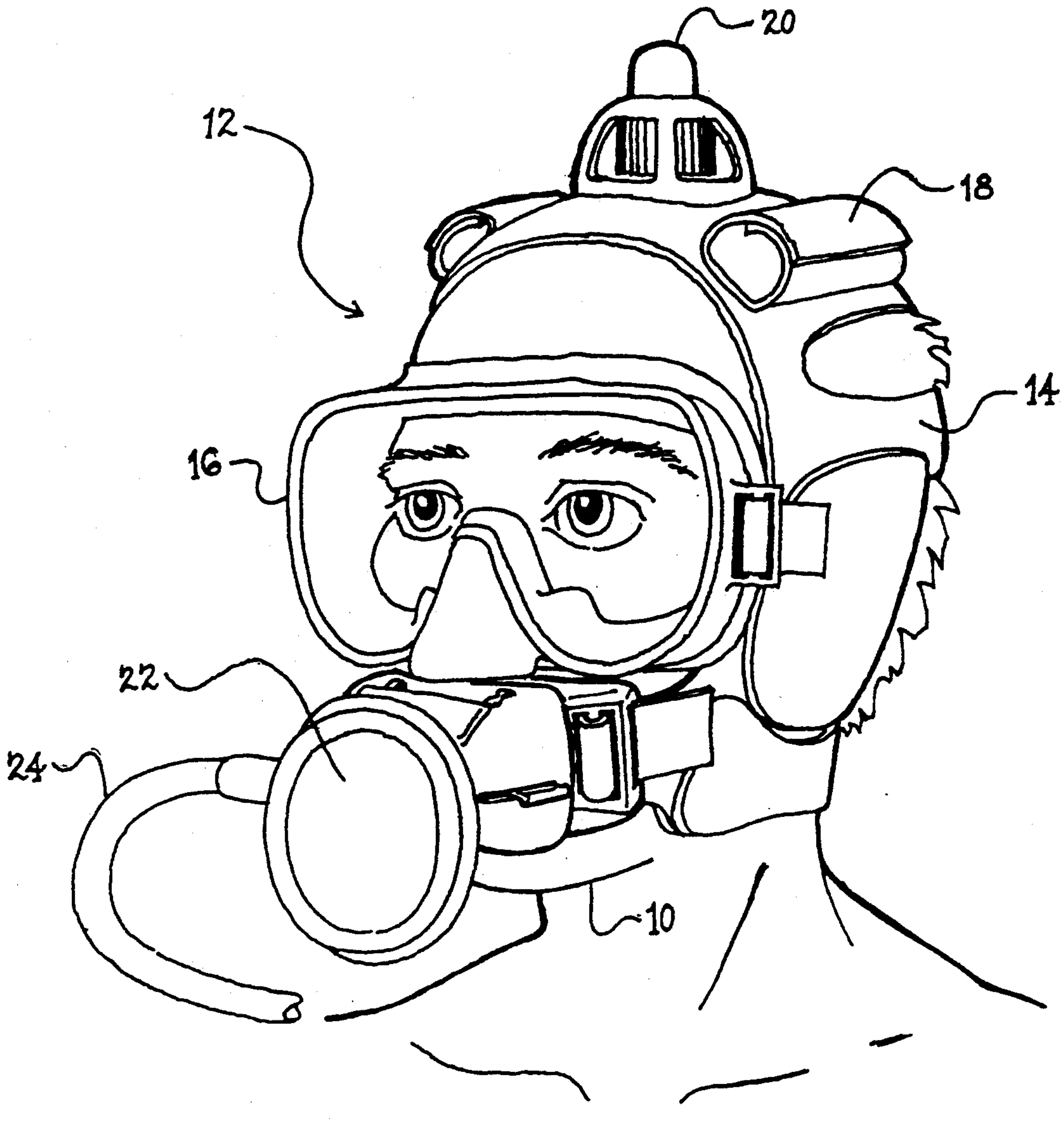
FIG. 1 is a perspective illustration of a diver wearing the breathing apparatus.

The breathing apparatus is shown at 10 in FIG. 1. The apparatus is strapped to the head of a diver 12 who is wearing a cap or helmet 14 having integral straps which retain the breathing apparatus 10 as well as a mask 16. The cap also mounts flashlight mounting sleeves 18 and a visual alarm 20 which is connected to monitors which keep track of the vital functions of the diver. The ear flaps of the cap would ordinarily mount headphones connected to the diver's communication system.

Whereas FIG. 1 illustrates the general environment in which the invention is used, this disclosure and the appended claims pertains to the breathing apparatus 10 itself rather than the collateral structure. As can be seen in that Figure, the breathing apparatus 10 connects to the regulator 22 which is fed by the air supply hose 24 which shown leads to the diver's tank, not shown.

Figure 2:
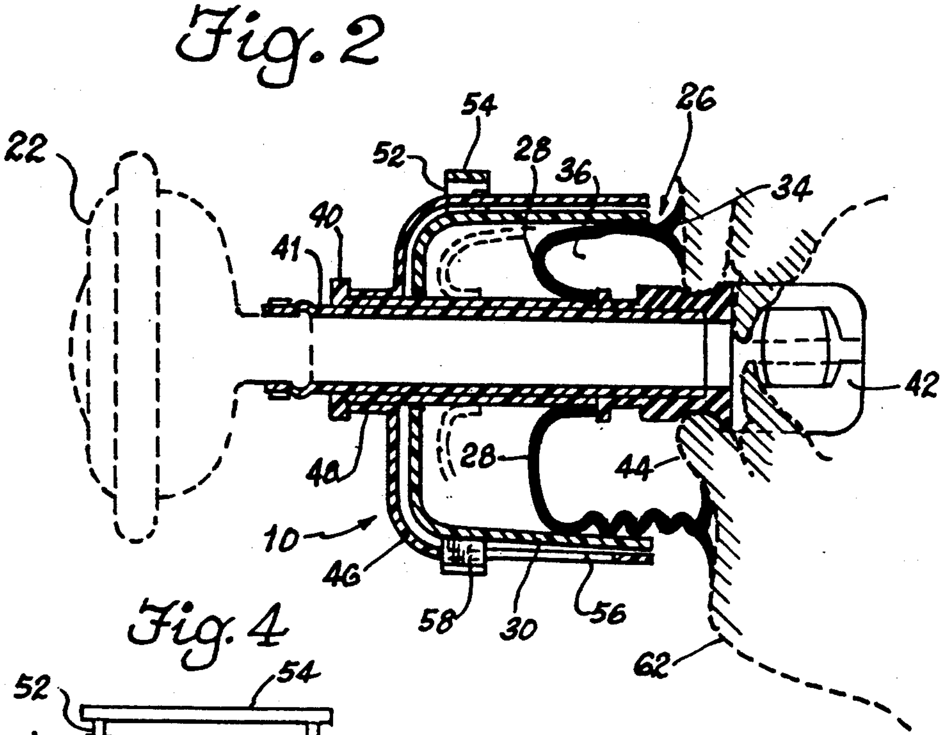
FIG. 2 is a longitudinal verticle section taken through the breathing apparatus illustrating an attached regulator in phantom.
Figure 4:
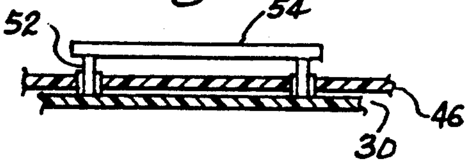
FIG. 4 is a detail partially in section, of the detent structure.
Figure 3:
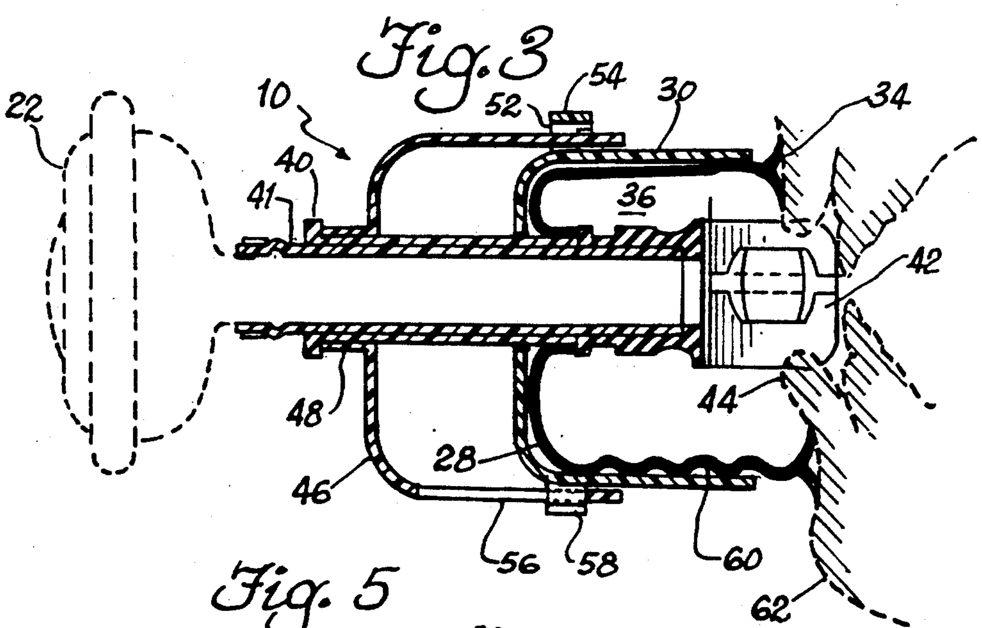
FIG. 3 is a longitudinal verticle section of the breathing apparatus identical to FIG. 2 except that the mouthpiece is in the retracted position.
Figure 5:
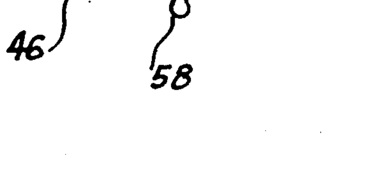
FIG. 5 is another partially sectional detail illustrating the guide slot construction.

Turning now to the breathing apparatus itself, as illustrated in FIGS. 2 through 9, at the core of the invention is a sealing cup 26 which actually has two main parts, the first being a internal, flexible diaphragm 28 and a second being a reinforcing frame 30 which is bonded to the diaphragm in a line around its periphery as indicated at 32 in FIG. 8. The continous edge of the diaphragm defines a split lip 34 which seals against the diver's face around the mouth, as shown in FIGS. 2 and 3. The flexible diaphragm defines an internal breathing chamber at 36 which compresses and expands according to the mode in which the unit is being used, as illustrated in FIGS. 2 and 3 respectively.

It is this sealing cup 26 which is connected to the head of the diver by a strap 38, which strap may also be attached to the diaphragm 28, or the diaphragm may have a seperate strap. In any event, in the preferred form, although not absolutely necessary, the two parts of the sealing cup are both strapped to the mouth of the diver.

As can be seen in FIGS. 2 and 3, in either mode of use, the frame 30 of the breathing cup remains in the same position vis-a-vis the face of the diver. It is the only element of the apparatus for which this is true. The rest of the apparatus moves in and out, toward and away from the face of the diver, except for the near portion of the diaphram which mounts the split lip 34.

At the heart of the unit is the airpipe 40. The airpipe 40 mounts the mouthpiece 42 at the diver's end. This mouthpiece is a standard diver's mouthpiece which is clamped between the teeth as shown in FIG. 2, with the lips sealing the breathing passageway from the surrounding water. However, as can be seen in FIG. 2, in this apparatus the seal between the diver's mouth and the ambient water is provided by the split lip 34 in addition to the diver's own lips 44. The outer end of the airpipe 40 is connected to the regulator 22, and in the mode of use shown in FIG. 2, air is delivered directly from the regulator through to the mouthpiece just as in a standard diving apparatus.

However, in actual use, the normal mode of use of the apparatus is not that shown in FIG. 2, which is the emergency mode, but is the configuration or mode indicated in FIG. 3. In this mode, the regulator, airpipe 40 and mouthpiece have been pulled forwardly, withdrawing the mouthpiece from the diver's mouth. FIG. 3 illustrates the right side of the mouthpiece, which is on the far side of the face, away from the teeth and lips as shown in the Figure, so that the mouth is completely clear to communicate into the breathing chamber 36. Somewhere in the breathing chamber, or between the diaphragm 28 and the frame 30, or in any other nearby suitable place, there is a microphone pick-up to transduce the voice of the diver for a sonar transmitter. The microphone, although being the cause behind the invention, is not itself part of the invention. As long as the apparatus is working well and the breathing chamber 36 is essentially free of water, the unit remains in the configuration shown in FIG. 3.

If the diver brushes against something or otherwise dislodges the apparatus momentarily so that it fills partially or completely with water, the diver pushes the regulator in, forcing the air tube and the attached mouthpiece into the mouth as shown in FIG. 2. When this occurs, the diaphragm 28, which is rigidly attached to the airpipe, follows the airpipe as shown in FIG. 2 from the phantom position to the position illustrated in hardline. Thus the air passage way, which formerly constituted air passing through the airpipe, through the mouthpiece and into the breathing chamber 36 where it was breathed by the diver, now comprises the straight passageway through the airpipe and the mouthpiece straight to the diver. Whatever water previously or currently occupies the breathing chamber 36 is not now a problem to the diver, who has a direct line through the airpipe to the air supply via the mouthpiece.

Although by properly constructing the materials thus far described the two respective modes of use shown in FIGS. 2 and 3 would be more or less stable, that is, once in one mode the apparatus would not seek the other mode, nonetheless, for positively establishment of the apparatus in the selected mode and for stablizing the unit against mutual rotational dislodgining about the longitudinal axis, a rigidifying/ detent means 46 is provided. The shell is bonded rigidly at its stub pipe 48 to the airpipe 40, so that it is non-rotational with the stub pipe, the mouthpiece and the sealing cup, 26. The airpipe actually comprises two telescoping pipes 40 and 41 which are bonded together. The shell has the two-fold purpose of further stablizing itself and the adjacent regulator relative to the other structure and in the above-stated rotational sense, and also establishing the parts into the mutual axial relationships necessary to define the two respective modes of use.

To accomplish these functions, the shell 46 is provided with a pair of longitudinally corrugated slots 50 as best seen in FIG. 6. A pair of detent posts 52 which extend upwardly from the frame 30 of the sealing cup slidingly engage in these corrugated slots. A crossbar 54 connects the tops of these two posts, and because the frame 30 is somewhat resilient as shown in FIG. 7, when the bar 54 is depressed, and the detent ribs on the sides of the post 52 clear the corrugations of the slots 50 permitting mutual sliding between the sealing cup 26 and the shell 46. When the crossbar 54 is released, the relative positions of the two members is fixed at that point.

This action permits the user to positively retain the mouthpiece in the mouth in the mode shown in FIG. 2, and positively retain the mouthpiece in the retractive position of FIG. 3. It will be recalled that the sealing cup 26 is strapped to the head of the diver, so that in FIG. 7, the sealing cup will be maintained securely around the mouth of the user in both modes. Only the shell 46, with its accompanying structure (the accompanying structure being everything in the apparatus except for the frame 30 and the front part of the diaphragm 28) will be permitted to move longitudinally.

In addition to the positive detent structure effected by the interengagement between the corrugated slots 50 and the post 52, rotational stability among the parts is furthered by the incorporation of longitudinally extended side slots 56 which ride on the ribs 58 of the frame 30. Naturally, these ribs and slots have the same basic longitudinal throw as do the corrugated slots 50 with the detent posts 52.

The corrugated slots and the straight slots that have been shown to stabilize the structure are exemplary only, and not intended to be limiting. Any other guide or detent structure that has the effect of achieving the desired stabilization would likely be acceptable.

When the apparatus is used in its communication mode, that is, the mouthpiece is retracted from the diver's mouth as shown in FIG. 3, the ribbed or accordianed lower wall 60 permits fairly free movement both in-and-out and up-and-down of the lower jaw 62, providing substantially complete "freedom of speech" for the diver. The diaphragm 24 is very flexible so that the seal around the mouth is good, and the frame 30 bonded peripherally to the diaphragm provides the form needed for the diaphragm to conform to the basic contours of the face. Of course, lower wall 60 could be made of any highly flexible material to permit the free movement of the jaw.

As diving becomes more and more sophisticated, communication between and among divers, the mother boat, and transducer bouys will undoubtly become more common and popular. The popularity and increase in use of submerged communication apparatuses has heretofore been limited not by the absence of the communication technology itself, but the inadequacies of the interface between the diver and the transducer, namely, inadequacies in the portion of the face mask covering the mouth. It is believed that the advances in this field presented by this invention will considerably further the popularity and extent of use of underwater communication devices, both amoung sport divers who need it both for sociability and safety, and for commercial divers who are increasingly required to use communications in reservoir and off-shore exploratory and salvage dives.

It is hereby claimed:

1. An air delivery apparatus for delivering air to the mouth of a diver comprising:

(a) a sealing cup having a sealing lip to seal around the mouth of the diver and define a breathing chamber adjacent to the mouth;

(b) a mouthpiece disposed at least partially within said breathing chamber and being movable from a position engaged in the mouth for delivering air thereto to a position retracted from the mouth exposing the mouth to communication with said breathing chamber; and, (c) an air delivery system for connecting between an external air supply and both said breathing chamber and said mouthpiece, such that air is provided to the diver through said mouthpiece when same is in the mouth, and through said breathing chamber when said mouthpiece is retracted from the mouth;

(d) said air delivery system including a substantially rigid airpipe passing through said sealing cup to said mouthpiece and communicating with said breathing chamber through said mouthpiece when said mouthpiece is retracted from the mouth;

(e) said sealing cup including a substantially flexible diaphragm which defines said breathing chamber, said diaphragm defining said sealing lip and being sealed around said airpipe; and, (f) said sealing cup including a reinforcing frame attached to said diaphragm adjacent said sealing lip to substantially maintain the shape of said diaphram around the mouth, said airpipe being slidable in a longitudinal direction substantially free of radial play with respect to said frame.

2. An apparatus according to claim 1 and including a detent for detaining said frame and said airpipe at at least two different mutual sliding positions defining a mouthpiece active mode and a retracted mouthpiece mode.

3. An apparatus according to claim 2 wherein said detent structure includes a substantially rigid shell which selectively overfits said reinforcing frame and said shell and frame have interfitting structure defining detent structure.

4. An apparatus according to claim 3 wherein said detent structure comprises at least one longitudinally extending corrugated slot defined in said shell and a ribbed member defined on said frame which extends into said slot and is slidable therein.

5. An apparatus according to claim 4 wherein said shell defines a plurality of longitudinal slots therein and said frame defines a plurality of ribs slidably seated in said slots to stabilize said shell and said frame against mutual rotation about a longitudinal axis.

6. An apparatus according to claim 5 and including strap means for retaining said sealing cup to the mouth of the diver.

7. An air delivery apparatus for delivering air to the mouth of a diver comprising:

(a) a sealing cup for sealing around the mouth of the diver and defining a breathing chamber adjacent to the mouth;

(b) said sealing cup including a rigid frame and means for retaining said rigid frame with said sealing cup to the head of a diver;

(c) a diver's mouthpiece;

(d) an airpipe connected to said mouthpiece and extending forward from the diver through said sealing cup to connect to an air supply, said mouthpiece being retractable on said airpipe from the mouth of the diver into said sealing cup such that said mouthpiece communicates with said breathing chamber to provide air to a diver without the mouthpiece being in the mouth of the diver; and, (e) guide means mounting said airpipe to said sealing cup substantially writing the motion of said airpipe to a longitudinal direction.

8. An air delivery apparatus for delivering air to the mouth of a diver comprising:

(a) a sealing cup for sealing around the mouth of the diver and defining a breathing chamber adjacent to the mouth;

(b) means for retaining said sealing cup to the head of a diver;

(c) a diver's mouthpiece;

(d) an airpipe connected to said mouthpiece and extending forward from the diver through said sealing cup to connect to an air supply, said mouthpiece being retractable on said airpipe from the mouth of the diver into said sealing cup such that said mouthpiece communicate with said breathing chamber to provide air to a diver without the mouthpiece being in the mouth of the diver;

(e) said sealing cup including a flexible diaphragm defining a sealing lip sealing around the mouth of the user such that said diaphram deforms when said mouthpiece is retracted on said pipe from the mouth to continuously maintain said breathing chamber airtight as said mouthpiece is moved into or out of the mouth;

(f) an outer shell rigid with said airpipe and overfitting said breathing cup and defining a longitudinally operable detent structure to establish at least two different longitudinal spacings of said airpipe, mouthpiece and shell relative to the face of the diver.

9. An apparatus according to claim 8 and including slotted guide means defined in said shell slidably seating guide ribs extending from said seating cup to retain rotational rigidity about the longitudinal axis between said shell and said sealing shell.

10. An apparatus according to claim 8 wherein said diaphragm has an accordioned lower side to increase diaphragm flexibility at the diver's jaw region to enhance the diver's freedom of speech.

11. An air delivery apparatus for delivering air to the mouth of a diver comprising:

(a) a sealing cup for sealing around the mouth of the diver and defining a breathing chamber adjacent to the mouth;

(b) said sealing cup including a rigid frame and means for retaining said frame and sealing cup to the head of a diver;

(c) a diver's mouthpiece;

(d) an airtube connected to said mouthpiece and extending forward from the diver through said sealing cup to connect to an air supply;

(e) rigid guide means mounted to said airpipe for guiding the airpipe through said sealing cup to make said mouthpiece retractable with said airpipe from the mouth of the diver into said sealing cup into a stable position, said guide means further for supporting said airpipe and mouthpiece on said guide means and frame such that said airpipe and mouthpiece will maintain their orientation relative to said rigid frame without assistance from the diver.

* * * * *